(12) United States Patent
Zhao

(10) Patent No.: US 9,789,046 B2
(45) Date of Patent: Oct. 17, 2017

(54) WATER-BASED RESIN NAIL POLISH

(71) Applicant: LES FINS NETWORK TECHNOLOGY CO., LTD., Hangzhou (CN)

(72) Inventor: Ming Zhao, Hangzhou (CN)

( * ) Notice: Subject to any disclaimer, the term of this patent is extended or adjusted under 35 U.S.C. 154(b) by 0 days.

(21) Appl. No.: 15/186,544

(22) Filed: Jun. 20, 2016

(65) Prior Publication Data

US 2017/0035670 A1 Feb. 9, 2017

Related U.S. Application Data

(63) Continuation of application No. PCT/CN2015/095156, filed on Nov. 20, 2015.

(30) Foreign Application Priority Data

Aug. 3, 2015 (CN) .......................... 2015 1 0468336

(51) Int. Cl.
| | | |
|---|---|---|
| A61K 8/49 | (2006.01) |
| A01N 43/90 | (2006.01) |
| A61K 8/34 | (2006.01) |
| A61K 8/39 | (2006.01) |
| A61K 8/41 | (2006.01) |
| A61K 8/73 | (2006.01) |
| A61K 8/81 | (2006.01) |
| A61K 8/87 | (2006.01) |
| A61Q 3/02 | (2006.01) |

(52) U.S. Cl.
CPC .............. *A61K 8/49* (2013.01); *A01N 43/90* (2013.01); *A61K 8/345* (2013.01); *A61K 8/39* (2013.01); *A61K 8/41* (2013.01); *A61K 8/731* (2013.01); *A61K 8/8147* (2013.01); *A61K 8/8182* (2013.01); *A61K 8/87* (2013.01); *A61Q 3/02* (2013.01); *A61K 2800/42* (2013.01); *A61K 2800/594* (2013.01); *A61K 2800/805* (2013.01); *A61K 2800/95* (2013.01)

(58) Field of Classification Search
None
See application file for complete search history.

*Primary Examiner* — Susan Tran
*Assistant Examiner* — William Craigo
(74) *Attorney, Agent, or Firm* — Wayne & Ken, LLC; Tony Hom

(57) ABSTRACT

The present invention relates to water-based resin nail polish, which comprises the following components in parts by weight: 48 to 53 parts of deionized water, 23 to 28 parts of polyurethane-35, 15 to 20 parts of acrylic acid/VP cross-linked polymer, 0.5 to 1 part of laureth-21 and 0.01 to 0.05 part of compound of formula I. The present invention is environment-friendly, non-toxic, harmless to human bodies and pollution-free to an environment.

10 Claims, No Drawings

WATER-BASED RESIN NAIL POLISH

CROSS-REFERENCE TO RELATED APPLICATIONS

This application is a continuation of International Patent Application No. PCT/CN2015/095156 with a filing date of Nov. 20, 2015, designating the United States, now pending, and further claims priority to Chinese Patent Application No. 201510468336.5 with a filing date of Aug. 3, 2015. The content of the aforementioned applications, including any intervening amendments thereto, are incorporated herein by reference.

TECHNICAL FIELD

The present invention relates to a cosmetic product, in particular to water-based resin nail polish.

BACKGROUND OF THE PRESENT INVENTION

Traditional nail polish contains a great amount of irritative chemical components such as acetone, methylbenzene, etc. and easily causes the dryness, yellowing and fragileness of fingernails, thereby influencing the health of the human bodies and polluting the environment.

The nail polish should have the characteristics of quickness in drying, glossiness, high adhesion, water resistance, easiness in coating and easiness in removal, and although a nail polish technology has already been considerably developed as the development of the science and technology, there are fewer materials meeting the above-mentioned performance requirements of the nail polish. So far, almost all the nail polish sold in the market including the nail polish produced by large international companies consists of nitrocellulose, modified resin, plasticizer and various mixed solvents, while solvents capable of dissolving the nitrocellulose are generally substances that are easy to volatilize and have irritation and strong toxicity. In recent years, as the popularization of the nail polish and the emergence of the nail art, there are more and more reports about the harm of the nail polish on the human bodies.

SUMMARY OF PRESENT INVENTION

The object of the present invention is to provide water-based resin nail polish which is environment-friendly, non-toxic, harmless to the human bodies and pollution-free to the environment.

The above-mentioned technical object of the present invention is realized through the following technical solution: the water-based resin nail polish comprises the following raw materials in parts by weight:

48 to 53 parts of deionized water, 23 to 28 parts of polyurethane-35, 15 to 20 parts of acrylic acid/VP cross-linked polymer, and 0.5 to 1 part of laureth-21, wherein the compound of formula I is shown as the following formula:

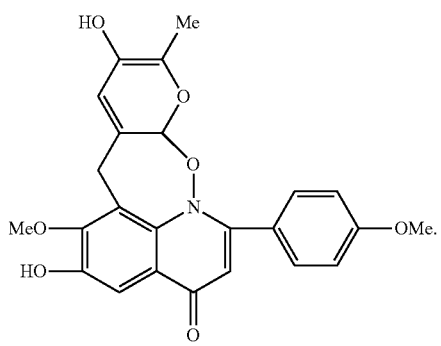

Preferably, the water-based resin nail polish further comprises the following raw material in parts by weight: 5 to 8 parts of functional monomer.

Preferably, the water-based resin nail polish further comprises the following raw materials in parts by weight: 3 to 5 parts of hydroxypropyl methylcellulose, 0.8 to 1 part of triethanolamine, 0.3 to 1.5 parts of glycerinum and 1.5 to 5.5 parts of coloring agent.

Preferably, the water-based resin nail polish further comprises the following raw materials in pails by weight: 3 to 5 parts of hydroxypropyl methylcellulose, 0.8 to 1 part of triethanolamine, 0.3 to 1.5 parts of glycerinum and 1.5 to 5.5 parts of coloring agent.

Another object of the present invention is to provide a preparation method of the water-based resin nail polish, which comprises the following steps:

(1) measuring 30 to 35 parts of deionized water; keeping the temperature at 60° C.-80° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; and after mixing, pressurizing and keeping standing for 1 h-2 h at 30° C.-40° C., wherein the pressure is 1 Mpa-2 Mpa, thereby forming a first mixture:

(2) mixing the residual deionized water and the laureth-21 at 40° C.-50° C. to form a second mixture;

(3) uniformly adding the first mixture into the second mixture in 20 minutes-30 minutes; always keeping the temperature at 70° C.-90° C.; during the mixing of the first mixture and the second mixture, continuously stirring; after the first mixture is completely added into the second mixture, continuing the stirring for 1 h-2 h; then keeping the temperature and the pressure for 2 h-4 h, wherein the temperature is kept at 80° C.-85° C. and the pressure is 0.5 Mpa-0.8 Mpa, and naturally cooling to form a finished product.

Yet another object of the present invention is to provide a preparation method of the water-based resin nail polish, which comprises the following steps:

(1) measuring 30 to 35 parts of deionized water; keeping the temperature at 60° C.-80° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; and after mixing, keeping the temperature at 70° C.-80° C.; adding 0.05 to 0.08 part of functional monomer; continuing the stirring for 10 minutes-20 minutes; then cooling to 30° C.-40° C.; pressurizing and keeping standing for 1 h-2 h, wherein the pressure is 1 Mpa-2 Mpa, thereby forming a first mixture;

(2) mixing the residual deionized water and the laureth-21 at 40° C.-50° C. to form a second mixture;

(3) uniformly adding the first mixture into the second mixture in 20 minutes-30 minutes; always keeping the temperature at 70° C.-90° C.; during the mixing of the first mixture and the second mixture, continuously stirring; after the first mixture is completely added into the second mixture, continuing the stirring for 1 h-2 h; then keeping the temperature and the pressure for 2 h-4 h, wherein the temperature is kept at 80° C.-85° C. and the pressure is 0.5 Mpa-0.8 Mpa, and naturally cooling to form a finished product.

Yet another object of the present invention is to provide a preparation method of the water-based resin nail polish, which comprises the following steps:

(1) uniformly mixing and stirring the hydroxypropyl methylcellulose and the triethanolamine to form a third mixture for standby application;

(2) measuring 30 to 35 parts of deionized water; keeping the temperature at 60° C.-80° C.; adding the polyurethane-35, the acrylic acid/VP cross-linked polymer and 0.01 to 0.05 part of the compound of formula 1 into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; and after mixing, pressurizing and keeping standing for 1 h-2 h at 30° C.-40° C., wherein the pressure is 1 Mpa-2 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes; always keeping the temperature at 70° C.-90° C.; during the mixing of the first mixture and the second mixture, continuously stirring; and after the first mixture is completely added into the second mixture, continuing the stirring for 1 h-2 h; then keeping the temperature and the pressure for 2 h-4 h, wherein the temperature is kept at 80° C.-85° C., and the pressure is 0.5 Mpa-0.8 Mpa;

(5) uniformly adding the third mixture into the mixture obtained in step (4) in 1 h-2 n, keeping the temperature at 60° C.-70° C., continuously stirring and uniformly mixing, after the third mixture is completely added and uniformly mixed, keeping the temperature and the pressure for 2 h-4 h, wherein the temperature is 65° C.-70° C., and the pressure is 0.8 Mpa-0.8 Mpa;

(6) adding the glycerinum and the coloring agent into the mixture obtained in the step (5); keeping the temperature at 80° C.-90° C.; uniformly stirring, and naturally cooling to obtain a nail polish finished product.

Yet another object of the present invention is to provide a preparation method of the water-based resin nail polish, which comprises the following steps:

(1) uniformly mixing and stirring the hydroxypropyl methylcellulose and the triethanolamine to form a third mixture for standby application;

(2) measuring 30 to 35 parts of deionized water; keeping the temperature at 60° C.-80° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; after mixing, keeping the temperature at 70° C.-80° C.; adding the functional monomer; continuing the stirring for 10 minutes-20 minutes; then re-cooling to 30° C.-40° C.; and pressurizing and keeping standing for 1 h-2 h at 30° C.-40° C., wherein the pressure is 1 Mpa-2 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes: always keeping the temperature at 70° C.-90° C., during the mixing of the first mixture and the second mixture, continuously stirring; and after the first mixture is completely added into the second mixture, continuing the stirring for 1 h-2 h, then keeping the temperature and the pressure for 2 h-4 h, wherein the temperature is kept at 80° C.-85° C., and the pressure is 0.5 Mpa-0.8 Mpa;

(5) uniformly adding the third mixture into the mixture obtained in step (4) in 1 h-2 h, keeping the temperature at 60° C.-70° C., continuously stirring and uniformly mixing, after the third mixture is completely added and uniformly mixed, keeping the temperature and the pressure for 2 h-4 h, wherein the temperature is 65° C.-70° C., and the pressure 0.6 Mpa-0.8 Mpa:

(6) adding the glycerinum and the coloring agent into the mixture obtained in the step (5), keeping the temperature at 80° C.-90° C.; uniformly stirring, and naturally cooling to obtain a nail polish finished product.

Preferably, a preparation method of the triethanolamine comprises:

(1) feeding ethylene oxide and ammonia water into a reactor, and performing a condensation reaction to generate a mixed solution of monoethanolamine, diethanolamine and triethanolamine under the reaction temperature of 35° C.-38° C. and the reaction pressure of 100 kPa-300 kPa;

(2) dehydrating and concentrating the mixed solution at 100° C.-110° C., then sending same into three decompression rectifying towers to perform the decompression rectification, and intercepting fractions according to different boiling points to obtain a triethanolamine semi-finished product;

(3) distilling the triethanolamine semi-finished product by using water vapor to remove impurities, adding sodium hydroxide for transforming the triethanolamine into an alkali metal salt to be precipitated, separating, then neutralizing, and then carrying out reduced pressure distillation to obtain a triethanolamine pure product.

Preferably, a preparation method of the hydroxypropyl methylcellulose comprises:

(1) soaking refined cotton cellulose in alkaline liquor for half an hour at 50° C.-60° C.; taking out the cotton cellulose; squeezing the cotton cellulose; pulverizing the cellulose, and properly aging the cellulose at 40° C.-50° C.;

(2) adding the alkali cellulose into an etherification kettle, sequentially adding epoxypropane and chloromethane, performing the etherification for 6 h-7 h at 55° C.-70° C., and keeping the pressure at 1.5 MPa-2 MPa;

(3) adding an appropriate amount of hydrochloric acid and oxalic acid into hot water at 70° C.-80° C. to wash materials; facilitating the swelling in volume; dehydrating by using a centrifugal machine; washing until the material is neutral, and when the water content in the material is lower than 60%, drying the material with hot air flow of higher than 130° C. until the water content is less than 5%.

In conclusion, the present invention has the following beneficial effects: the content of volatile organic compounds in the water-based resin nail polish prepared by the present invention is less than 15 g/L; the water-based resin nail polish contains no substance such as methylbenzene, formaldehyde, ethyl acetate, DBP, etc. and is non-toxic, odorless, harmless to the human bodies, pollution-free to the environment, short in drying time, good in adhesion and water resistance under the fusion action of various raw materials, high in film glossiness, bright in color and high in color retention; moreover, the process of the present invention is unique; during the mixing of the polyurethane-35 and the acrylic acid/VP cross-linked polymer, the raw materials are added in a step-by-step manner, so that two materials can be sufficiently mixed and cross-linked in a stirring way under a specific temperature; the subsequent temperature and pressure keeping process facilitates the improvement of molecular activity, further facilitates the better fusion of two materials and eliminates the stress generated by the combination of the two materials; and by adding the functional monomer, the water resistance and the adhesion of the nail polish can be improved. In the formula of the present invention, the compound of formula I extracted from ginkgo leaves is added, so that the breeding of the fingernail fungus can be effectively prevented.

DETAILED DESCRIPTION OF PREFERRED EMBODIMENTS

The present invention is further described below through the embodiments. It shall be appreciated that the method as described in the embodiments of the present invention is only used for describing the present invention rather than limiting the present invention. On the premise of the concept of the present invention, simple improvements to the preparation method of the present invention belong to the protection scope claimed by the present invention. All raw materials, solvents and strains used in the embodiments are purchased from the company of Sigma Biochemical and Organic Compounds for Research and Diagnostic Clinical Reagents.

Preparation Embodiment of the Compound of Formula I:

As raw materials, the ginkgo leaves are pulverized, soaked in ethanol and extracted for 2 times-4 times for 12 h-72 h each time, and the extracting solutions are merged, filtered and concentrated to obtain a ginkgo leaves extract, wherein the weight ratio of the ethanol to the ginkgo leaves is 3-4: 1.

After being dissolved in acetone, the ginkgo leaves extract is mixed with 60-mesh-120-mesh silica gel which is 2 times-5 times of the weight of the extract; the ginkgo leaves extract is packed in columns in a dry method; then the gradient elution by using gradient chloroform-methanol solutions with the volume ratio sequentially of 9:1, 8:2, 7:3, 6:4 and 5:5 is performed; the elution solution obtained by virtue of elution through the chloroform-methanol solution with the volume ratio of 9:1 is collected and called a first elution solution: the above-mentioned elution solution is continuously separated by using silica gel chromatography; gradient elution by using the chloroform-acetone solutions with volume ratios sequentially of 15:1, 1:1, 5:1 and 2:1 is performed; and the elution solution obtained by virtue of elution through the chloroform-acetone solution with the volume ratio of 10:1 is called a second elution solution. The above-mentioned second elution solution is continuously separated by using silica column chromatography and then is gradiently eluted by using petroleum ether-ethyl acetate solutions with the volume ratio sequentially of 9:1, 8:2, 7:3, 6:4 and 5:5, wherein the elution solution obtained by using the petroleum ether-ethyl acetate solution with the volume ratio of 7:3 is called a third elution solution.

The above-mentioned third elution solution is introduced into a high pressure liquid-phase chromatography (inverted-phase preparation chromatography at pressure of 5 Mpa-15 Mpa) to be separated and purified: the high pressure liquid-phase chromatography adopts a $C_{18}$ chromatographic column of 21.2 mm*250 mm and 5 µm; the mobile phase is a 60 wt % methanol aqueous solution, and the flow rate of the mobile phase is 12 mL/min; the detection wavelength of the ultraviolet detector is 374 nm; the third elution solution is sampled for 60 µL-150 µL at each time; the elution solution corresponding to the chromatographic peak retention time of 31 min after the sampling at each time is collected, and after solvent is removed, the compound of formula I

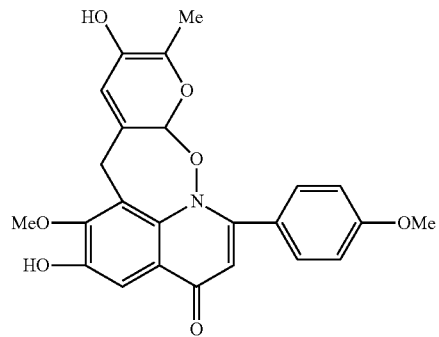 [SMILES: COc1ccc(-c2cc(=O)c3cc(O)c(OC)c4c3n2OC2OC(C)=C(O)C=C2C4)cc1]

is obtained.

After being obtained, the compound of the formula I can be re-dissolved in the methanol solution, the methanol solution is used as the mobile phase, the chromatographic separation can be carried out through a gel column, and the compound of the formula I can be further purified.

The compound of the formula I is yellow powder; and the main structure characteristic peaks of an ultraviolet spectrum, an infrared spectrum and a hydrogen nuclear magnetic resonance spectroscopy of the compound of formula I are listed hereinafter.

The ultraviolet spectrum (the solvent is methanol): $\lambda_{max}$ (log $\epsilon$)210(4.36), 266(3.82), 374(3.68)nm;

The infrared spectrum (potassium bromide pellet): $\nu_{max}$3452, 2924, 2615, 1668, 1612, 1516, 1437, 1316, 1247, 1182, 1083, 1022, 868, 722 cm$^{-1}$;

$^1$H NMR (500 MHz, CDCl$_3$, ppm) δ:10.7 (s —OH), 9.48 (s —OH) 6.28-7.52 (d, —CH 5H), 6.57 (s, 1H), 6.18 (s 1H), 3.27 (d, —CH$_2$), 1.99-3.81 (d, —CH$_3$ 9H).

Embodiment 1:

The water-based resin nail polish comprises the following raw materials in parts by weight:
- 52.36 parts of deionized water,
- 27.41 parts of polyurethane-35,
- 19.41 parts of acrylic acid/VP cross-linked polymer,
- 0.82 part of laureth-21, and
- 0.01 part of compound of formula I.

The preparation method of the water-based resin nail polish of the present embodiment comprises the following steps:

(1) measuring 35 parts of deionized water; keeping the temperature at 60° C.-80° C., preferably 75° C.; adding the polyurethane-35, the acrylic acid/VP cross-linked polymer and the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes, preferably about 20 minutes; continuously stirring in the adding process for uniformly mixing two materials in the deionized water; and then pressurizing and keeping standing for 1 h-2 h, preferably 1.8 h, at 30° C.-40° C., preferably 35° C., wherein the pressure is 1 Mpa-2 Mpa, preferably 1.8 Mpa, thereby forming a first mixture;

(2) mixing the residual deionized water and the laureth-21 at 40° C.-50° C., preferably 45° C., to form a second mixture;

(3) uniformly adding the first mixture into the second mixture in 20 minutes-30 minutes; always keeping the temperature at 70° C.-90° C.; during the mixing of the first mixture and the second mixture, continuously stirring; after the first mixture is completely added into the second mixture, continuing the stirring for 1 h-2 h, preferably 2 h; then keeping the temperature and the pressure for 2 h-4 h, preferably 3.5 h, wherein the temperature is kept at 80° C.-85° C., the pressure is 0.5 Mpa-0.8 Mpa, preferably 0.7 Mpa, thereby naturally cooling to form a finished product.

The present embodiment is transparent in water color; obtained from performance detection, the present embodiment has good water resistance and adhesion, and the water absorption rate is lower than 3.6%; the conventional properties are detected as follows: the nail polish is uniformly smeared as far as possible in an ordinary coating manner; the temperature is 32° C., the humidity is 50%, and the seawater in Yalongwan Resort Area of Sanya is used for soaking; all washing adopts an ordinary washing way to respectively simulate the bath hand dirt removal housework doing and swimming; the ordinary alkaline soap water is adopted; and the ordinary laundry powder is adopted, and Diaopai washing powder is adopted in the present experiment.

After being dried for 30 minutes, under a normal-temperature washing condition, the coating film has no color change in 60 minutes and does not drop off; under the washing condition of warm water at 40° C., the coating film has no color change and does not drop off in 60 minutes; under a soapy water washing condition, the coating film has no color change in 20 minutes and does not drop off; under the laundry powder washing condition, the coating film has no change in 60 minutes and does not drop off; under the seawater soaking condition, the coating film has no color change in 80 minutes and does not drop off; and under the accidental collision, the coating film drops off.

Embodiment 2:

The water-based resin nail polish comprises the following raw materials in parts by weight:
- 53 parts of deionized water,
- 28 parts of polyurethane-35,
- 20 parts of acrylic acid/VP crosslinked polymer,
- 1 part of laureth-21, and
- 0.02 part of compound of formula I.

The preparation method of the present embodiment is similar to that of the embodiment 1, and property parameters are approximate to those of the embodiment I.

Embodiment 3:

The water-based resin nail polish comprises the following raw materials in parts by weight:
- 48 parts of deionized water,
- 23 parts of polyurethane-35,
- 15 parts of acrylic acid/VP cross-linked polymer,
- 0.5 part of laureth-21 and
- 0.03 part of compound of formula I.

The preparation method of the present embodiment is similar to that of the embodiment 1, and property parameters are approximate to those of the embodiment I.

Embodiment 4:

The water-based resin nail polish comprises the following raw materials in parts by weight:
- 53 parts of deionized water,
- 28 parts of polyurethane-35,
- 20 parts of acrylic acid/VP cross-linked polymer,
- 1 part of laureth-21,
- 0.04 part of compound of formula I, and
- 8 parts of functional monomer, and the functional monomer can be acrylic amide.

The preparation method of the present embodiment comprises the following steps:

(1) measuring 30 parts of deionized water; keeping the temperature at 60° C.-80° C., preferably 75° C.; adding the polyurethane-35, propylene, the acrylic acid/VP cross-linked polymer and the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes: continuously stirring in the adding process for uniformly mixing two materials in the deionized water; after mixing, keeping the temperature at 70° C.-80° C.; adding the functional monomer; continuing the stirring for 10 minutes-20 minutes; re-cooling to 30° C.-40° C.; pressurizing and keeping standing for 1 h-2 h, preferably 2 h, wherein the pressure is 1 Mpa-2 Mpa, preferably 1.8 Mpa, thereby forming a first mixture;

(2) mixing the residual deionized water and the laureth-21 at 40° C.-50° C. to form a second mixture;

(3) uniformly adding the first mixture into the second mixture in 20 minutes-30 minutes; always keeping the temperature at 70° C.-90° C., preferably 80° C.; during the mixing of the first mixture and the second mixture, continuously stirring; after the first mixture is completely added into the second mixture, continuing the stirring for 1 h-2 h, preferably 2 h; then keeping the temperature and the pressure for 2 h-4 h, preferably 3.5 h, wherein the temperature is kept at 80° C.-85° C., the pressure is 0.5 Mpa-0.8 Mpa, preferably 0.6 Mpa, thereby naturally cooling to form a finished product.

The present embodiment is transparent in water color; obtained from performance detection, the present embodiment has good water resistance and adhesion, and the water absorption rate is lower than 2.5%; by adding and reducing the addition amount of the functional monomer, it is discovered that the water resistance is relatively good when the addition amount of the functional monomer is 5 to 8 parts; when the addition amount is 8 parts, the water resistance is optimum, and when the addition amount goes beyond the range of 5 to 8 parts, the water absorption rate is obviously increased; the conventional properties are detected as follows: the nail polish is uniformly smeared as far as possible in an ordinary coating manner; the temperature is 32° C., the humidity is 50%, and the seawater in Yalongvvan Resort Area of Sanya is used for soaking, all washing adopts an ordinary washing way to respectively simulate the bath, hand dirt removal, housework doing and swimming; the ordinary alkaline soap water is adopted; and the ordinary laundry powder is adopted, and Diaopai washing powder is adopted in the present experiment.

After being dried for 30 minutes, under a normal-temperature washing condition, the coating film has no color change in 60 minutes and does not drop off; under the washing condition of warm water at 40° C., the coating film has no color change and does not drop off in 60 minutes; under a soapy water washing condition, the coating film has no color change in 20 minutes and does not drop off; under the laundry powder washing condition, the coating film has no change in 60 minutes and does not drop off; under the seawater soaking condition, the coating film has no color change in 80 minutes and does not drop off; and under the accidental collision, the coating film drops off.

Embodiment 5:

The water-based resin nail polish comprises the following raw materials in parts by weight:

48 parts of deionized water,
23 parts of polyurethane-35,
15 parts of acrylic acid/VP cross-linked polymer,
0.5 part of laureth-21,
0.05 part of compound of formula I, and
6 parts of functional monomer, and the functional monomer can be acrylic amide.

The preparation method of the present embodiment is similar to that of the embodiment 4, and property parameters are approximate to those of the embodiment 4.

Embodiment 6:

The water-based resin nail polish comprises the following raw materials in parts by weight:

49.76 parts of deionized water,
24.01 parts of polyurethane-35,
16.38 parts of acrylic acid/VP cross-linked polymer,
0.76 part of laureth-21,
0.02 part of compound of formula I,
4.21 parts of hydroxypropyl methylcellulose,
0.99 part of triethanolamine,
0.78 part of glycerine, and
3.11 parts of coloring agent, including 3.1 part of red coloring agent, and 0.01 part of black coloring agent, The preparation method of the present embodiment comprises the following steps:

(1) uniformly mixing and stirring the hydroxypropyl methylcellulose and the triethanolamine to form a third mixture for standby application;

(2) measuring 32 parts of deionized water; keeping the temperature at 60° C.-80° C., preferably at 70° C.; adding the polyurethane-35, the acrylic acid/VP cross-linked polymer and the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; after mixing, pressurizing and keeping standing for 1 h-2 h, preferably 1.8 h, at 30° C.-40° C., preferably 35° C., wherein the pressure is 1 Mpa-2 Mpa, preferably 1.8 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes; always keeping the temperature at 70° C.-90° C., preferably 85° C.; during the mixing of the first mixture and the second mixture, continuously stirring; after the first mixture is completely added into the second mixture, continuing the stirring for 1 h-2 h; and then keeping the temperature and the pressure for 2 h-4 h, preferably 3.5 h, wherein the temperature is kept at 80° C.-85° C., and the pressure is 0.5 Mpa-0.8 Mpa;

(5) uniformly adding the third mixture into the mixture obtained in step (4) in 1 h-2 h; keeping the temperature at 60° C.-70° C.; continuously stirring and uniformly mixing; and after the third mixture is completely added and uniformly mixed, keeping the temperature and the pressure for 2 h-4 h, preferably 3.5 h, wherein the temperature is 65° C.-70° C., and the pressure is 0.6 Mpa-0.8 Mpa;

(6) adding the glycerinum and the coloring agent into the mixture obtained in the step (5), keeping the temperature at 80° C.-90° C.; uniformly stirring, and naturally cooling to obtain a nail polish finished product.

The present embodiment is transparent in dark true red; obtained from performance detection, the present embodiment has good water resistance and adhesion, and the water absorption rate is lower than 3.3%; the conventional properties are detected as follows: the nail polish is uniformly smeared as far as possible in an ordinary coating manner; the temperature is 32° C., the humidity is 50%, and the seawater in Yalongwan Resort Area of Sanya is used for soaking; all washing adopts an ordinary washing way to respectively simulate the bath, hand dirt removal, housework doing and swimming; the ordinary alkaline soap water is adopted; and the ordinary laundry powder is adopted, and Diaopai washing powder is adopted in the present experiment.

After being dried for 30 minutes, under a normal-temperature washing condition, the coating film has no color change in 60 minutes and does not drop off; under the washing condition of warm water at 40° C., the coating film has no color change and does not drop off in 60 minutes; under a soapy water washing condition, the coating film has no color change in 20 minutes and does not drop off; under the laundry powder washing condition the coating film has no change in 60 minutes and does not drop off; under the seawater soaking condition, the coating film has no color change in 80 minutes and does not drop off; and under the accidental collision, the coating film drops off.

Embodiment 7:

The water-based resin nail polish comprises the following raw materials in parts by weight:

53 parts of deionized water,
28 parts of polyurethane-35,
20 parts of acrylic acid/VP cross-linked polymer,
1 part of laureth-21,
0.03 part of compound of formula I,
5 parts of hydroxypropyl methylcellulose,
1 part of triethanolamine,
1.5 parts of glycerine, and
5.5 parts of coloring agent, wherein the coloring agent is selected according to needs.

The preparation method of the present embodiment is similar to that of the embodiment 6, and property parameters are approximate to those of the embodiment 6, Embodiment 8:

The water-based resin nail polish comprises the owing raw materials in parts by weight:
  48 parts of deionized water,
  23 parts of polyurethane-35,
  15 parts of acrylic acid/VP cross-linked polymer,
  0.5 part of laureth-21,
  0.04 part of compound of formula I,
  3 parts of hydroxypropyl methylcellulose,
  0.8 part of triethanolamine,
  0.3 part of glycerine, and
  1.5 parts of coloring agent, wherein the coloring agent is selected according to needs.

The preparation method of the present embodiment is similar to that of the embodiment 6, and property parameters are approximate to those of the embodiment 6.

Embodiment 9:

The water-based resin nail polish comprises the following raw materials in parts by weight:
  49.76 parts of deionized water,
  24.01 parts of polyurethane-35,
  16.38 parts of acrylic acid/VP cross-linked polymer,
  0.76 part of laureth-21,
  0.02 part of compound of formula I,
  4.21 parts of hydroxypropyl methylcellulose,
  0.99 part of triethanolamine,
  0.78 part of glycerine,
  3.11 parts of coloring agent, including 3.1 part of red coloring agent, and 0.01 part of black coloring agent, and
  7 parts of functional monomer, wherein the functional monomer can be acrylic amide.

The preparation method of the present embodiment comprises the following steps:

(1) uniformly mixing and stirring the hydroxypropyl methylcellulose and the triethanolamine to form a third mixture for standby application;

(2) measuring 33 parts of deionized water: keeping the temperature at 60° C.-80° C., preferably 70° C.; adding the polyurethane-35, the acrylic acid/VP cross-linked polymer and the compound of formula I into the deionized water, wherein the adding manner is to add the polyurethane-35, the acrylic acid/VP cross-linked polymer and the compound of formula according to a time slot, the time interval at each time is 3 minutes-5 minutes, and the addition is completed in 15 minutes-20 minutes; continuously stirring in the adding process for uniformly mixing two materials in the deionized water; after mixing, keeping the temperature at 70° C.-80° C.; then adding the functional monomer: continuing the stirring for 10 minutes-20 minutes; re-cooling to 30° C.-40° C.; and pressurizing and keeping standing for 1 h-2 h, preferably 2 h, wherein the pressure is 1 Mpa-2 Mpa, preferably 1.8 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes; always keeping the temperature at 70° C.-90° C.; during the mixing of the first mixture and the second mixture, continuously stirring; after the first mixture is completely added into the second mixture, continuing the stirring for 1 h-2 h; and then keeping the temperature and the pressure for 2 h-4 h, preferably 3.5 h, wherein the temperature is kept at 80° C.-85° C., and the pressure is 0.5 Mpa-0.8 Mpa;

(5) uniformly adding the third mixture into the mixture obtained in step (4) in 1 h-2 h; keeping the temperature at 60° C.-70° C.; continuously stirring and uniformly mixing; and after the third mixture is completely added and uniformly mixed, keeping the temperature and the pressure for 2 h-4 h, preferably 3.5 h, wherein the temperature is 65° C.-70° C., preferably 70° C., and the pressure is 0.6 Mpa-0.8 Mpa, preferably 0.7 Mpa;

(6) adding the glycerinum and the coloring agent into the mixture obtained in the step (5), keeping the temperature at 80° C.-90° C.; uniformly stirring, and naturally cooling to obtain a nail polish finished product.

The present embodiment is transparent in dark true red; obtained from performance detection, the present embodiment has good water resistance and adhesion, and the water absorption rate is lower than 2.3%; the conventional properties are detected as follows: the nail polish is uniformly smeared as far as possible in an ordinary coating manner: the temperature is 32° C., the humidity is 50%, and the seawater in Yalongwan Resort Area of Sanya is used for soaking; all washing adopts an ordinary washing way to respectively simulate the bath, hand dirt removal, housework doing and swimming; the ordinary alkaline soap water is adopted; and the ordinary laundry powder is adopted, and Diaopai washing powder is adopted in the present experiment.

After being dried for 30 minutes, under a normal-temperature washing condition, the coating film has no color change in 60 minutes and does not drop off; under the washing condition of warm water at 40° C., the coating film has no color change and does not drop off in 60 minutes; under a soapy water washing condition, the coating film has no color change in 20 minutes and does not drop off; under the laundry powder washing condition, the coating film has no change in 60 minutes and does not drop off; under the seawater soaking condition, the coating film has no color change in 80 minutes and does not drop off: and under the accidental collision, the coating film drops off.

Embodiment 10:

The water-based resin nail polish comprises the following raw materials in parts by weight:
  51.38 parts of deionized water,
  24.21 parts of polyurethane-35,
  16.36 parts of acrylic acid/VP cross-linked polymer.
  0.76 part of laureth-21,
  0.04 part of compound of formula I,
  4.21 parts of hydroxypropyl methylcellulose,
  0.99 part of triethanolamine,
  0.42 part of glycerine, and
  1.67 parts of coloring agent, including 1.64 parts of white coloring agent, 0.01 part of yellow coloring agent, 0.01 part of red coloring agent, and 0.01 part of black coloring agent.

The preparation method of the present embodiment is similar to that of the embodiment 6, the color is light cameo brown and property parameters are approximate to those of the embodiment 6.

Embodiment 11:

The water-based resin nail polish comprises the following raw materials in parts by weight:
  48.72 parts of deionized water,
  22.53 parts of polyurethane-35,
  16.38 parts of acrylic acid/VP cross-linked polymer,
  0.76 part of laureth-21,
  0.05 part of compound of formula I,
  4.21 parts of hydroxypropyl methylcellulose, 0.99 part of triethanolamine,
0.28 part of glycerine, and
5.13 parts of coloring agent, including 5.12 parts of white coloring agent, and 0.01 part of black coloring agent, The preparation method of the present embodiment is similar to that of the embodiment 6, the color is cinerous, and property parameters are approximate to those of the embodiment 6.

Embodiment 12:

The water-based resin nail polish comprises the following raw materials in parts by weight:
51.13 parts of deionized water,
24.46 parts of polyurethane-35,
16.39 parts of acrylic acid/VP cross-linked polymer.
0.78 part of laureth-21,
0.02 part of compound of formula I,
4.29 parts of hydroxypropyl methylcellulose,
0.99 part of triethanolamine,
0.4 part of glycerine, and
1.58 parts of coloring agent, including 1.53 parts of white coloring agent, and 0.05 part of red coloring agent, The preparation method of the present embodiment is similar to that of the embodiment 6, the color is light pink, and property parameters are approximate to those of the embodiment 8.

Embodiment 13: Preparation Method of Triethanolamine Involved in the Embodiments 6-12:

(1) feeding ethylene oxide and ammonia water into a reactor, and performing a condensation reaction to generate a mixed solution of monoethanolamine, diethanolamine and triethanolamine under the reaction temperature of 35° C.-38° C. and the reaction pressure of 100 kPa-300 kPa;

(2) dehydrating and concentrating the mixed solution at 100° C.-110° C., then sending same into three decompression rectifying towers to perform the decompression rectification, and intercepting fractions according to different boiling points to obtain a triethanolamine semi-finished product;

(3) distilling the triethanolamine semi-finished product by using water vapor to remove impurities: adding sodium hydroxide for transforming the triethanolamine into an alkali metal salt to be precipitated separating, and then neutralizing; and then carrying out reduced pressure distillation to obtain a triethanolamine pure product.

The triethanolamine prepared by the method is relatively high in purity which can reach 99.5% or more.

A preparation method of the involved hydroxypropyl methylcellulose comprises:

(1) soaking refined cotton cellulose in alkaline liquor for half an hour at 50° C.-60° C., taking out the cotton cellulose, squeezing same, pulverizing the cellulose, and properly aging the cellulose at 40° C.-50° C.;

(2) adding the alkali cellulose into an etherification kettle, sequentially adding epoxypropane and chloromethane, performing the etherification for 6 h-7 h at 55° C.-70° C., and keeping the pressure at 1.5 MPa-2 MPa;

(3) adding an appropriate amount of hydrochloric acid and oxalic acid into hot water at 70° C.-80° C. to wash materials, facilitating the swelling in volume, dehydrating by using a centrifugal machine, washing until the material is neutral, and when the water content in the material is lower than 60%, drying the material with hot air flow of higher than 130° C. until the water content is less than 5%.

Activity Experiments:

1. Activity Experiment for the Compound of Formula I

Bacteria (*Trichophyton rubrum, Trichophyton gypsum* and flocculent trichomementagrophytes) are suspended in an MH culture medium, the dispersion concentration is about 105 cfu·mL−1, the bacterial solution is added onto 96-pore plate (100 μL of the bacterial solution is added into each pore), the culture medium is used as a blank control, DMSO is used for substituting a test material as a negative control, and itraconazole (Xian-Janssen Pharmaceutical Ltd.) is used as a positive control. The compound of formula I is dissolved in DMSO to respectively prepare solutions of 800 μg·mL$^{-1}$, 400 μg·mL$^{-1}$, 200 μg·mL$^{-1}$, 100 μg·mL$^{-1}$, 50 μg·mL$^{-1}$ and 25 μg·mL$^{-1}$ (for the further experiment that MIC$_{50}$ is less than 5 μg·mL$^{-1}$, the concentration gradient of the prepared solution is 50 μg·mL$^{-1}$, 25 μg·mL$^{-1}$, 12.5 μg·mL$^{-1}$, 5.25 μg·mL$^{-1}$, 3.1 μg·mL$^{-1}$ and 1.5 μg·mL$^{-1}$), the prepared solution is added to the 96-pore plate according to the quantity that each pore is filled with 11 μL of the solution [the final concentration of the medicinal solution is respectively 80 μg·mL$^{-1}$, 40 μg·mL$^{-1}$, 20 μg·mL$^{-1}$, 10 μg·mL$^{-1}$, 5 μg·mL$^{-1}$ and 2.5 μg·mL$^{-1}$ (for the further experiment that the MIC$_{50}$ is less than 5 μg·mL$^{-1}$, the final concentration of the medicinal solution is 5 μg·mL$^{-1}$, 2.5 μg·mL$^{-1}$, 1.25 μg·mL$^{-1}$, 0.63 μg·mL$^{-1}$, 0.31 μg·mL$^{-1}$ and 0.15 μg·mL$^{-1}$], and four parallel experiments are performed for each concentration gradient. The 96-pore plate is placed into an incubator at 37° C. to be cultured for 24 h, then 25 μL of the prepared solution containing 4 mg of PBS of MTT for each mL is added into each hole, and the solution is cultured for 4 h under a same condition, 100 μL of SDS lysis solution (including 95 mL of triple-distilled, 10 g of SDS, 5 mL of isopropyl alcohol and 0.1 mL of concentrated hydrochloric acid) is added into each pore and then is cultured for 12 h. An enzyme labeling instrument is used for determining an OD value at 570 nm, and a percent inhibition rate is calculated according to the formula equation:

$$I\% = 100 - \frac{OD_{test}}{OD_{control}} \times 100$$

The activity is expressed by the semi-inhibition rate MIC50; when the MIC$_{50}$ is smaller, the activity of the compound is higher, and a result is that: the semi-inhibition rate MIC$_{50}$ of the compound of formula I on *Trichophyton rubrum, Trichophyton gypsum* and flocculent trichomementagrophytes is respectively 0.63, 0.60 and 0.82; and the semi-inhibition rate MIC$_{50}$ of itraconazole on *Trichophyton rubrum, Trichophyton gypsum* and flocculent trichomementagrophytes is respectively 0.63, 0.70 and 0.65.

2. Activity Experiment for Preparations:

By using the preparations of embodiments 1-5, the activity experiment is performed as follows:

A small piece which is 0.5 mm thick and 1.5 cm*3 cm is cut off from a corner portion of an ox horn, and half a side surface is treated by using the preparations of the embodiments 1-5 once a day continuously for five days. Then the small piece of ox horn is fixed on a metal column which is about 0.5 cm above the surface of water-containing agar in a damp room, and the treated half side surface faces downwards. The whole side surface, facing upwards, of the ox horn is inoculated with a microconidium suspension of Trichophyton mentagrophytes in a dot manner. Then the bacterial colony form is stored for 10 days at 28° C.

Half a back surface of the ox horn is pretreated for 5 times by using the preparations of the embodiments 1-5, so that the germination of fungal spores on a whole top surface is completely prevented. Even after 90 days, an inoculation spot can be observed from the whole top surface under a microscope. Therefore, the preparations of the embodiments 1-5 containing the compound of formula I can effectively prevent the fungi growth.

A control experiment is conducted according to the above-mentioned method, and the difference is that the preparations of the embodiments 1-5 do not contain the compound of formula I, and fewer growth spots of the fungi are observed on the treated side surface of the ox horn, while good growth of the fungi is observed on the other half piece of the ox horn.

After a blank piece which is not treated by the preparations of the present invention is inoculated, the fungi adequately grow on the surface of the ox horn.

I claim:

1. Water-based resin nail polish, characterized by comprising the following raw materials in parts by weight:
   48 to 53 parts of deionized water,
   23 to 28 parts of polyurethane-35,
   15 to 20 parts of acrylic acid/VP cross-linked polymer,
   0.5 to 1 part of laureth-21, and
   0.01 to 0.05 part of compound of formula I,
   wherein the compound of formula I is shown as the following formula:

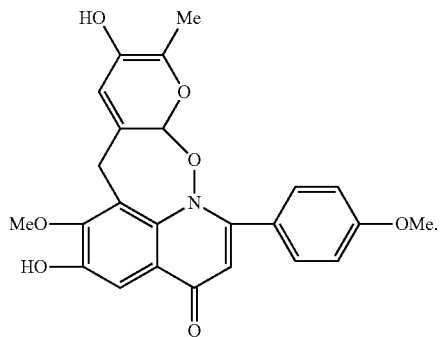

I

2. The water-based resin nail polish according to claim 1, characterized by further comprising the following raw material in parts by weight: 5 to 8 parts of functional monomer.

3. The water-based resin nail polish according to claim 1, characterized by further comprising the following raw materials in parts by weight:
   3 to 5 parts of hydroxypropyl methylcellulose,
   0.8 to 1 part of triethanolamine,
   0.3 to 1.5 parts of glycerinum and
   1.5 to 5.5 parts of coloring agent.

4. The water-based resin nail polish according to claim 2, characterized by further comprising the following raw materials in parts by weight: 3 to 5 parts of hydroxypropyl methylcellulose, 0.8 to 1 part of triethanolamine, 0.3 to 1.5 parts of glycerinum and 1.5 to 5.5 parts of coloring agent.

5. A preparation method of the water-based resin nail polish according to claim 1, characterized by comprising the following steps:
   (1) measuring 30 to 50 parts of deionized water; keeping the temperature at 60-80° C; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing, two materials in the deionized water: and after mixing, pressurizing and keeping standing for 1 h-2 h at 30° C.-40° C., wherein the pressure is 1 Mpa-2 Mpa, thereby forming a first mixture;
   (2) mixing the residual &ionized water and the laureth-21 at 40° C.-50° C. to form a second mixture;
   (3) uniformly adding the first mixture into the second mixture in 20-30 minutes, always keeping the temperature at 70° C.-90° C.; during the mixing of the first mixture and the second mixture, continuously stirring; after the first mixture is completely added into the second mixture, continuing the stirring for 1 h-2 h; then keeping the temperature and the pressure for 2 h-4 h, wherein the temperature is kept at 80° C.-85° C. and the pressure is 0.5 Mpa-0.8 Mpa, and naturally cooling to form a finished product.

6. The preparation method of the water-based resin nail polish according to claim 2, characterized by comprising the following steps:
   (1) measuring 30 to 50 parts of deionized water; keeping the temperature at 60° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minutes-5 minutes, and the addition is completed in 15 minutes-20 minutes; continuously stirring in the adding process for uniformly mixing two materials in the deionized water; and after mixing, keeping the temperature at 70° C.-80° C.; adding the functional monomer; continuing the stirring for 10 minutes-20 minutes; then cooling to 30° C.-40° C.; pressurizing and keeping standing for 1 h-2 h, wherein the pressure is 1 Mpa-2 Mpa, thereby forming a first mixture;
   (2) mixing the residual deionized water and the laureth-21 at 40° C.-50° C. to form a second mixture;
   (3) uniformly adding the first mixture into the second mixture in 20 minutes-30 minutes; always keeping the temperature at 70° C.-90° C.; during the mixing of the first mixture and the second mixture, continuously stirring; after the first mixture is completely added into the second mixture, continuing the stirring for 1 h-2 h; then keeping the temperature and the pressure for 2 h-4 h, wherein the temperature is kept at 80° C.-85° C. and the pressure is 0.5 Mpa- 0.8 Mpa, and naturally cooling to form a finished product.

7. The preparation method of the water-based resin nail polish according to claim 3, characterized by comprising the following steps:
   (1) uniformly mixing and stirring the hydroxypropyl methylcellulose and the triethanolamine to form a third mixture for standby application;
   (2) measuring 30 to 35 parts of deionized water; keeping the temperature at 60° C.-80° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3 minute-5 minutes, and the addition is completed in 15 minutes-20 minutes; continuously stirring in the adding process for uniformly mixing two materials in the deionized water; and after mixing, pressurizing and keeping standing for 1 h-2 h at 30° C.-40° C., wherein the pressure is 1 Mpa -2 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes; always keeping the temperature at 70° C.-90° C.; during the mixing of the first mixture and the second mixture, continuously stirring; and after the first mixture is completely added into the second mixture, continuing the stirring for 1 h-2 h, then keeping the temperature and the pressure for 2 h-4 h, wherein the temperature is kept at 80° C.-85° C., and the pressure is 0.5 Mpa-0.8 Mpa;

(5) uniformly adding the third mixture into the mixture obtained in step (4) in 1 h-2 h; keeping the temperature at 60° C.-70° C.; continuously stirring and uniformly mixing; after the third mixture is completely added and uniformly mixed, keeping the temperature and the pressure for 2 h-4 h, wherein the temperature is 65° C.-70° C., and the pressure is (0.6 Mpa-0.8 Mpa;

(6) adding the glycerinum and the coloring agent into the mixture obtained in the step (5); keeping the temperature at 80-90° C.; uniformly stirring, and naturally cooling to obtain a nail polish finished product.

8. The preparation method of the water-based resin nail polish according to claim 4, characterized by comprising the following steps:

(1) uniformly mixing and stirring the hydroxypropyl methylcellulose and the triethanolamine to form a third mixture for standby application;

(2) measuring 30 to 35 parts of deionized water; keeping the temperature at 60° C.-80° C.; adding the polyurethane-35, the acrylic acid/VP cross-linked polymer and 0.01 to 0.05 part of the compound of formula I into the deionized water, wherein the adding manner is to add the polyurethane-35, the acrylic acid/VP cross-linked polymer and the compound of formula I according to a time slot, the time interval at each time is 3-5 minutes, and the addition is completed in 15 minutes-20 minutes; continuously stirring in the adding process for uniformly mixing two materials in the deionized water; after mixing, keeping the temperature at 70° C.-80° C; adding the functional monomer; continuing the stirring for 10 minutes- 20 minutes; then cooling to 30° C-40° C.; and pressurizing and keeping standing for 1 h-2 h at 30° C.-40° C., wherein the pressure is 1 Mpa-2 Mpa, thereby forming a first mixture;

(3) mixing the residual deionized water and the laureth-21 at 40° C.-50° C. to form a second mixture;

(4) uniformly adding the first mixture into the second mixture in 20 minutes-30 minutes; always keeping the temperature at 70° C.-90° C.; during the mixing of the first mixture and the second mixture, continuously stirring; and after the first mixture is completely added into the second mixture, continuing the stirring, for 1 h-2 h; then keeping the temperature and the pressure for 2 h-4 h, wherein the temperature is kept at 80° C.-85° C., and the pressure is 0.5 Mpa-0.8 Mpa;

(5) uniformly adding the third mixture into the mixture obtained in step (4) in 1 h-2 h; keeping the temperature at 60° C.-70° C.; continuously stirring and uniformly mixing; and after the third mixture is completely added and uniformly mixed, keeping the temperature and the pressure for 2 h-4 h, wherein the temperature is kept at 65° C.-70° C., and the pressure is 0.6 Mpa-0.8 Mpa;

(6) adding the glycerinum and the coloring agent into the mixture obtained in the step (5); keeping the temperature at 80< C.-90° C.; uniformly stirring, and naturally cooling to, obtain a nail polish finished product.

9. The water-based resin nail polish according to claim 3, characterized in that a preparation method of the triethanolamine comprises:

(1) feeding ethylene oxide and ammonia water into a reactor, and performing a condensation reaction to generate a mixed solution of monoethanolamine, diethanolamine and triethanolamine under the reaction temperature of 35° C.-38° C. and the reaction pressure of 100 kPa-300 kPa;

(2) dehydrating and concentrating the mixed solution at 100° C.-110° C., then sending same into three decompression rectifying towers to perform the decompression rectification, arid intercepting fractions according to different boiling points to obtain a triethanolamine semi-finished product;

(3) distilling the triethanolamine semi-finished product by using water vapor to remove impurities, adding sodium hydroxide for transforming the triethanolamine into an alkali metal salt to be precipitated, separating, then neutralizing, and then carrying out reduced pressure distillation to obtain a triethanolamine pure product.

10. The water-based resin nail polish according t claim 3, characterized in that a preparation method of the hydroxypropyl methylcellulose comprises:

(1) soaking refined cotton cellulose in alkaline liquor for half an hour at 50° C.-60° C., taking out the cotton cellulose, squeezing same, pulverizing the cellulose, and properly aging the cellulose at 40° C.-50° C.;

(2) adding the alkali cellulose into an etherification kettle, sequentially adding epoxypropne and chloromethane, performing the etherification for 6 h-7 h at 55° C.-70° C., and keeping the pressure at 1.5 MPa-2MPa;

(3) adding an appropriate amount of hydrochloric acid and oxalic acid into hot water at 70° C. -80° C. to wash materials, facilitating the swelling in volume, dehydrating by using a centrifugal machine, washing until the material is neutral, and when the water content in the material is lower than 60% drying the material with hot air flow of higher than 130° C. until the water contents is less than 5%.

* * * * *